(12) United States Patent
Pestotnik et al.

(10) Patent No.: US 7,882,863 B2
(45) Date of Patent: Feb. 8, 2011

(54) APPARATUS AND METHOD FOR MIXING AND TRANSFERRING MEDICATIONS

(75) Inventors: David R. Pestotnik, Casper, WY (US); Christopher M Tice, Jackson, WY (US)

(73) Assignee: CD Solutions, LLC, Jackson, WY (US)

( * ) Notice: Subject to any disclaimer, the term of this patent is extended or adjusted under 35 U.S.C. 154(b) by 1147 days.

(21) Appl. No.: 11/551,175

(22) Filed: Oct. 19, 2006

(65) Prior Publication Data
US 2007/0088252 A1     Apr. 19, 2007

Related U.S. Application Data

(60) Provisional application No. 60/728,437, filed on Oct. 19, 2005.

(51) Int. Cl.
*B65B 1/04* (2006.01)
(52) U.S. Cl. ............................. 141/318; 141/9; 141/27; 141/301
(58) Field of Classification Search ............ 141/1, 141/2, 9, 21, 27, 301, 318, 320, 321; 604/27, 604/30, 32, 246
See application file for complete search history.

(56) References Cited

U.S. PATENT DOCUMENTS

| | | | |
|---|---|---|---|
| 4,822,339 A | 4/1989 | Tran | |
| 4,937,194 A * | 6/1990 | Pattillo et al. | 141/10 |
| 5,002,528 A * | 3/1991 | Palestrant | 604/28 |
| 5,211,632 A | 5/1993 | Tsukada | |
| 5,289,858 A * | 3/1994 | Grabenkort | 141/97 |
| 5,911,252 A * | 6/1999 | Cassel | 141/234 |
| 6,099,511 A * | 8/2000 | Devos et al. | 604/246 |
| 6,159,232 A * | 12/2000 | Nowakowski | 606/213 |
| 6,221,041 B1 * | 4/2001 | Russo | 604/82 |
| 6,238,372 B1 | 5/2001 | Zinger et al. | |
| 6,379,340 B1 | 4/2002 | Zinger et al. | |
| 7,418,981 B2 * | 9/2008 | Baker et al. | 141/9 |
| 7,749,189 B2 * | 7/2010 | Tennican et al. | 604/88 |
| 2002/0087118 A1 | 7/2002 | Reynolds et al. | |
| 2003/0036725 A1 | 2/2003 | Lavi et al. | |
| 2004/0254525 A1 | 12/2004 | Uber, III et al. | |

\* cited by examiner

*Primary Examiner*—Timothy L Maust
(74) *Attorney, Agent, or Firm*—Samuel M. Freund; Cochran Freund & Young LLC

(57) ABSTRACT

An apparatus and method for transferring a chosen quantity of medication from a vial to an intravenous infuser container under sterile conditions is described. The present invention further facilitates dissolving solid medications contained in the vial or diluting concentrated medications contained in the vial, and transferring the resulting solutions to the infuser container.

11 Claims, 4 Drawing Sheets

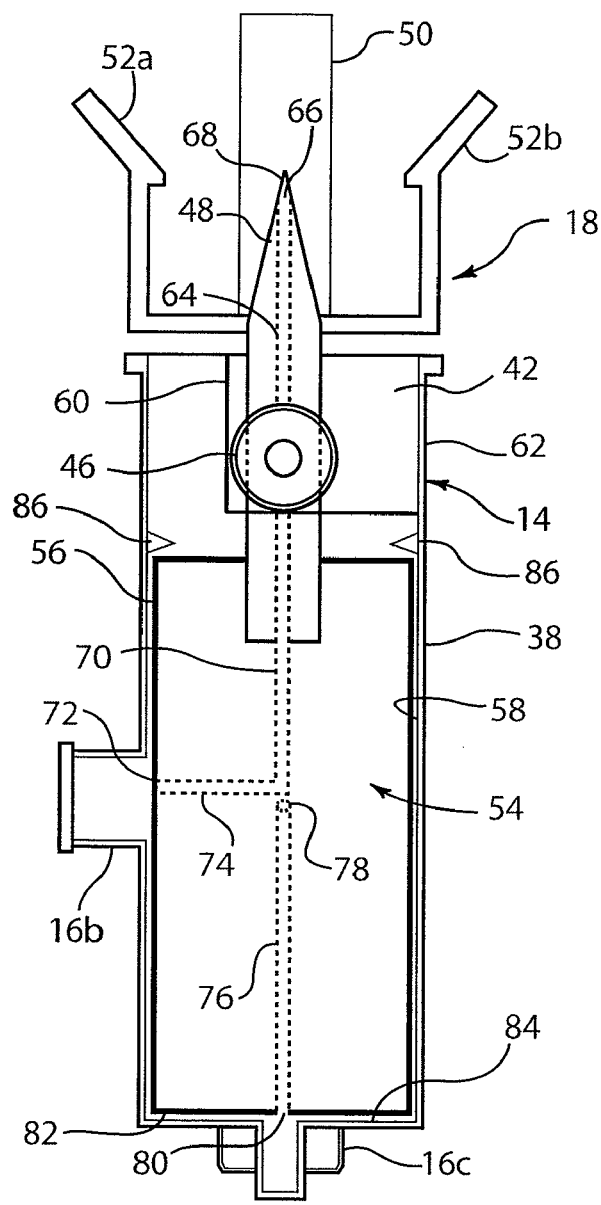
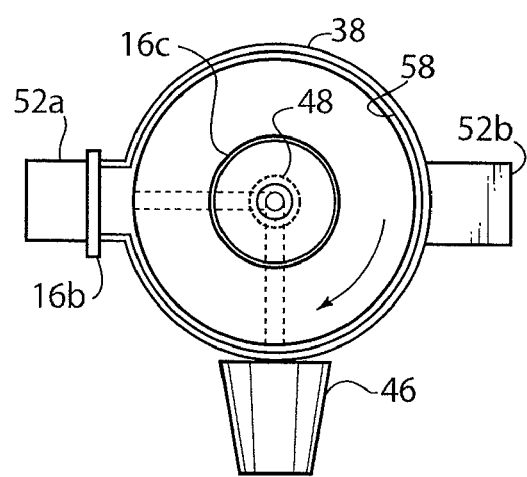
FIG. 3A
FIG. 3B

APPARATUS AND METHOD FOR MIXING AND TRANSFERRING MEDICATIONS

CROSS-REFERENCE TO RELATED APPLICATION

This application claims benefit of and priority to U.S. Provisional Patent Application Ser. No. 60/728,437 entitled "Apparatus and Method for Mixing and Transferring Medications" by David R. Pestotnik and Christopher M. Tice, filed Oct. 19, 2005, the entire contents of which are specifically incorporated herein by reference for all that it discloses and teaches.

FIELD OF THE INVENTION

The present invention relates generally to apparatus for mixing medications and, more particularly, to a device for transferring chosen quantities of medications into intravenous solution containers.

BACKGROUND OF THE INVENTION

Unstable medications are often stored in powdered form under inert gases, or as a concentrated liquid which may require refrigeration. Before use, the medication must be dissolved, diluted, and/or warmed. The processed medication has only short-term stability, and must be used rapidly. Premixed medications may be sent to a user by priority mail or other rapid shipping service; however, this adds significant cost to the user, and the delay incurred may reduce the effectiveness of the medication. Complicated mixing apparatus and protocols currently in use for mixing and diluting medications in a sterile environment have generated difficulty for patients who self-administer medications while housebound. Other situations which require medications to be mixed or diluted include trauma units, hospitals and doctor's offices where nurses and other medical staff must quickly and accurately mix medications while maintaining sterile conditions.

In U.S. Pat. No. 3,923,059 for "Medicament Injector," which issued to R. W. Ogle on Dec. 2, 1975, a device for expelling the contents of a vial into a solution container is described. The vial is preloaded at a central plant, used once at the time of injection into an intravenous bottle, and thereafter disposed of. There is no teaching therein for measuring a chosen amount of medication into the intravenous bottle, and storing the remaining material for later, repeated use, for diluting medications or for dissolving medications shipped as solids.

Accordingly, it is an object of the present invention to provide a device for transferring a chosen quantity of medication into a container for intravenous injection under sterile conditions.

Another object of the invention is to provide a device for diluting concentrated medications and transferring the diluted medication into a container for intravenous injection under sterile conditions.

Yet another object of the present invention is to provide a device for dissolving a chosen quantity of medication and transferring the solution into a container for intravenous injection under sterile conditions.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for transferring medications from a vial into an infuser container having a fill port hereof, includes: a three-way valve having a first port, a second port and a third port; means for connecting the vial to the first port such that fluids can be transferred between the vial and the three-way valve; a syringe; means for connecting the syringe to the second port such that fluids can be transferred between the syringe and the three-way valve; and means for connecting the fill port of the infuser container to the third port of the three-way valve such that fluids can be transferred between the three-way valve and the container.

In another aspect of the present invention, in accordance with its objects and purposes, the method for transferring solid medications in a vial into an infuser container having a fill port, hereof, includes the steps of: connecting the vial to one port of a three-way valve; connecting a syringe containing an effective amount of solvent for dissolving the solid medication to a second port of the three-way valve; connecting the infuser container to the third port of the three-way valve; transferring the solvent from the syringe to the vial through a pathway in the three-way valve connecting the syringe with the vial, thereby forming a solution; withdrawing the solution from the vial into the syringe through the pathway in the three-way valve connecting the syringe with the vial; and transferring the solution from the syringe to the infuser container through a pathway in the three-way valve connecting the syringe with the fill port of the infuser container.

In yet another aspect of the present invention, in accordance with its objects and purposes, the method for diluting liquid medications in a vial and transferring the diluted medications into an infuser container having a fill port, hereof, includes the steps of: connecting the vial to one port of a three-way valve; connecting a syringe containing a chosen amount of diluent to a second port of the three-way valve; connecting the infuser to the third port of the three-way valve; transferring the diluent from the syringe to the vial through a pathway in the three-way valve connecting the syringe with the vial, thereby forming a solution; withdrawing the solution from the vial into the syringe through the pathway in the three-way valve connecting the syringe with the vial; and transferring the solution from the syringe to the infuser container through a pathway in the three-way valve connecting the syringe with the fill port of the infuser container.

In still another aspect of the present invention, in accordance with its objects and purposes, the method for transferring liquid medications in a vial to an infuser container having a fill port, hereof, includes the steps of: connecting the vial to one port of a three-way valve; connecting an empty syringe to a second port of the three-way valve; connecting the infuser container to the third port of the three-way valve; transferring the liquid medication from the vial to the syringe through a pathway in the three-way valve connecting the vial with the syringe; and transferring the liquid medication from the syringe to the infuser container through a pathway in the three-way valve connecting the syringe with the fill port of the infuser container.

Benefits and advantages of the present invention include, but are not limited to, providing a device and method for accurately and rapidly mixing medical solutions and dissolving powdered medications, thereby forming solutions, and transferring these solutions into intravenous infuser containers while maintaining the sterility of both the starting materials and the final product, and using inexpensive components commonly available to medical personnel.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 3A is a schematic representation of a side cross section view of the three-way valve and the vial holding/piercing/transferring device of the present invention shown in FIG. 2 hereof, FIG. 3B is a schematic representation of a bottom cross section view thereof, FIG. 3C is a schematic representation of a top cross section view of the three-way valve and the vial holding/piercing/transferring device shown in FIG. 3A hereof, while

DETAILED DESCRIPTION OF THE INVENTION

Briefly, the present invention includes a closed apparatus for mixing, diluting and transferring sterile medications to an infuser container having a filling port. The mixing/diluting apparatus permits the dissolution of medications that are shipped and stored as solids, and the dilution of medications that are shipped and stored as concentrated liquids. Chosen doses of medications can also be introduced into the infuser container for self-dosing patient use as well as for other uses. The apparatus may be accurately and rapidly used, maintains the sterility of the medications, and may easily be assembled from readily available parts.

Reference will now be made in detail to the present embodiments of the invention, an example of which is illustrated in the accompanying drawings. In the FIGURES, similar or identical structure will be identified using identical callouts.

Figure 1:
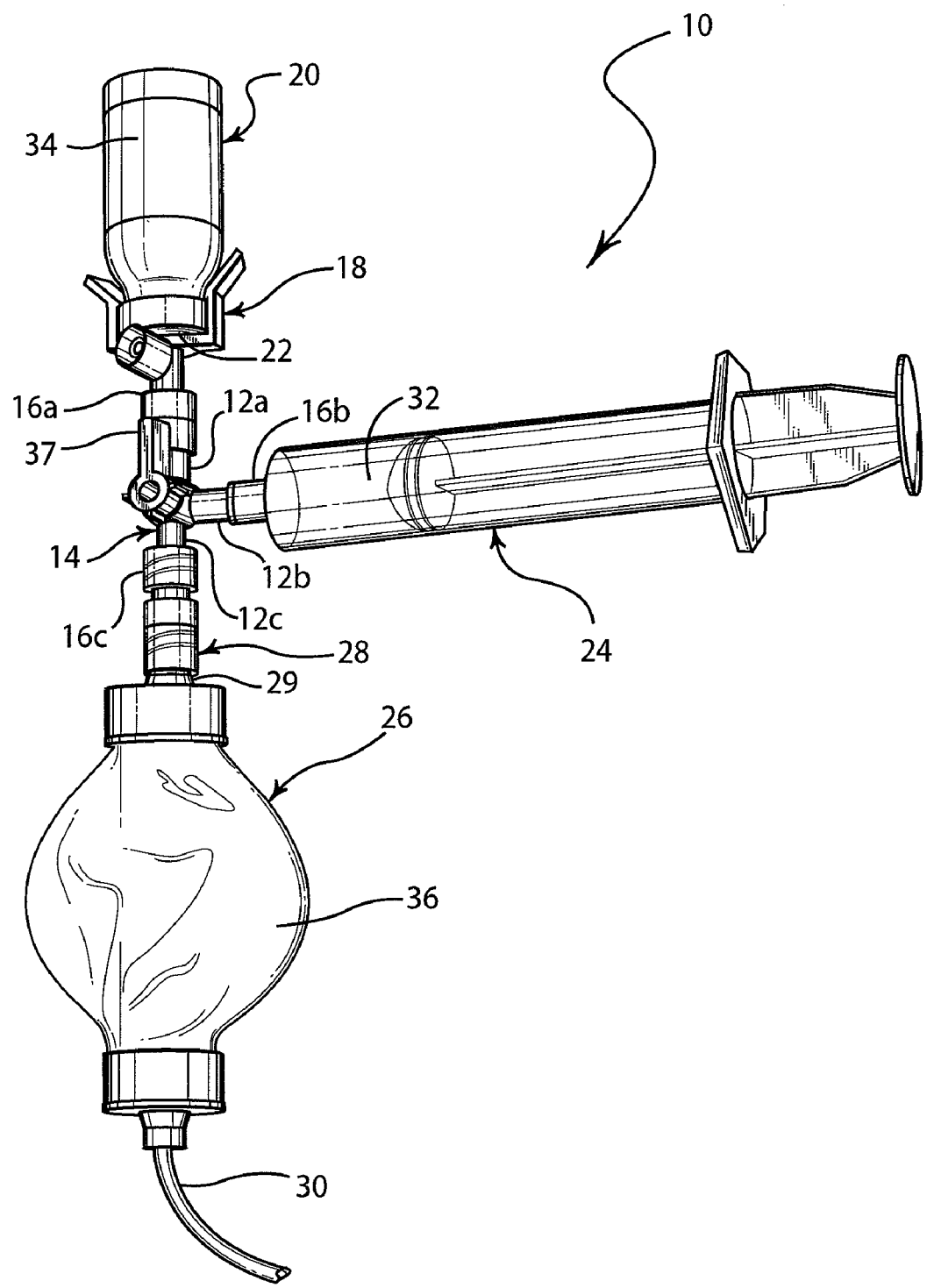
FIG. 1 is a schematic representation of a projection view of one embodiment of the present closed apparatus for mixing liquid medications and for dissolving powdered medications disposed in a vial, and introducing the resulting solutions into an infuser container, illustrating a commercially available three-way valve, means for connecting the vial to the valve such that materials can be transferred therebetween, a syringe connected to the valve such that materials can be transferred therebetween, and the fill port of the infuser container being connected to the valve such that materials can be transferred therebetween.

Turning now to the FIGURES, FIG. 1, a schematic representation of a projection view of apparatus, 10, of the present invention is shown. Each port, 12a, 12b and 12c of three-way valve, 14, may be fitted with Luer locking devices 16a, 16b, and 16c, to which are attached vial holding/piercing/transferring device, 18, which securely holds vial, 20, while piercing the elastomeric or rubber sealing port, 22, thereof, thereby permitting fluid transfer in and out of vial 20; syringe, 24; and infuser container, 26. In particular, syringe 24 may be connected either to vial 20 or infuser container, 26. Holding/piercing/transferring device 18 may include air vent, 27, for equalizing pressures, thereby reducing the pressure required to add liquids to vial 20. Infuser container 26 may be an elastomeric container, or may be constructed from other medically useful materials. Inlet, 28, of infuser container 26 may further be fitted with a one-way valve, 29. Outlet tube, 30, of infuser container 26 may be used for connecting to an intravenous line, a catheter or a shunt, as examples.

Syringe 24 may contain a solvent, 32, for the contents, 34, of vial 20, contain a diluent for the contents 34 of vial 20, or may be empty, as will be described in more detail hereinbelow. Infuser 26 may contain a solvent or carrier, 36, for the medication, such as saline solution, as an example. Valve handle, 37, of three-way valve 14 permits the ready access of the fluid pathway between vial 20 and syringe 24, and alternatively that between syringe 24 and infuser container 26. Graduation marks, 40, on syringe 24 permit the syringe to be filled with a chosen quantity of fluid.

Three-way valve 14, holding/piercing/transferring device 18, syringe 24, and infuser container 26 are all readily available components from medical and other component suppliers, and may be purchased with Luer-lock-compatible or other compatible fittings in sterile packaging. They may readily be assembled to form closed, sterile system 10, which is capable of providing several medication related functions. It should be mentioned that other methods for attaching these components to permit sterile transfer of fluids are contemplated. Several materials of construction for these components are contemplated depending on the manufacturer thereof and on specific user requirements. The use of apparatus 10 in accordance with the teachings of the present invention is described in the EXAMPLES set forth hereinbelow.

Figure 2:
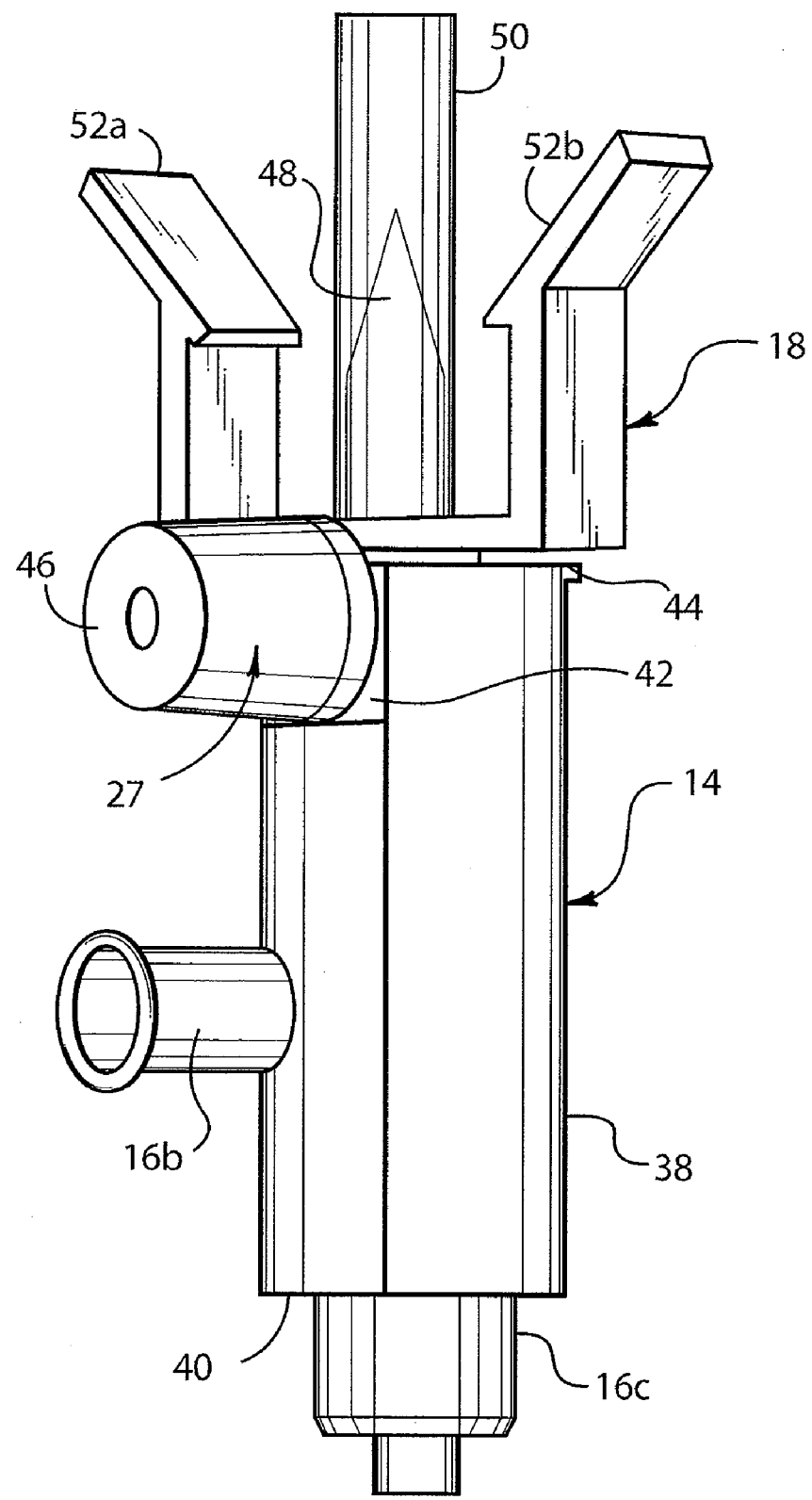
FIG. 2 is a schematic representation of a projection view of another embodiment of the three-way valve and the holding/piercing/transferring device for connecting the vial thereto.

FIG. 2 is a schematic representation of a projection view of another embodiment of three-way valve 14 and holding/piercing/transferring device 18 for connecting the vial thereto. Shown in FIG. 2 are outer cylindrical, 38, having closed lower end, 40, which may open into male Luer lock connection 16c or other suitable connector for establishing fluid flow capability to elastomeric infuser container 26 (not shown in FIG. 2), having female Luer lock connection 16b or other suitable connector for establishing fluid flow capability to syringe 24 (not shown in FIG. 2), and having slot, 42, in upper end, 44, thereof for engaging air vent 27, shown having cap, 46, thereon. Shown also is piercing spike, 48, for piercing sealing port 22 of vial 20 (not shown in FIG. 2), covered with safety device, 50, and vial securing arms, 52a and 52b.

FIG. 3A is a schematic representation of a side cross section view of three-way valve 14 and vial holding/piercing/transferring device 18 of the present invention shown in FIG. 2 hereof, showing inner solid cylinder, 54, rigidly attached to and in fluid communication with piercing spike, 48. Spike 48 is also rigidly attached to vial holding/piercing/dispensing device 18. Outer wall, 56, of inner cylinder 54 is adapted to make fluid seal contact with the inner wall, 58, of outer cylinder 38, yet be able to rotate therein when arms 52a and 52b are turned relative to outer cylinder 38. Walls, 60 and 62, of slot 42, which are located approximately 90° apart engage air vent cap 46, thereby preventing inner cylinder 54 from being rotated more than about 90° when holding/piercing/transferring device 18 is rotated.

Channel, 64, in the interior of spike 48 opens, 66, to the outside at or near tip, 68, thereof, is one terminus of first channel, 70, formed inside inner cylinder 54. The second terminus, 72, of first channel 70 opens through outer wall 56 of inner cylinder 54, whereby fluids may pass between vial 20 (not shown in FIG. 3A) through opening 66 and into syringe 24 (not shown in FIG. 3A) when inner cylinder 54 is located as shown in FIG. 3A. First channel 70 is shown having a bend, 74, in order to reach the entrance of female syringe Luer lock 16b. Second channel, 76, in inner cylinder 54 opens through outer wall 56 at terminus 78, and at terminus, 80, located at the bottom surface, 82 of inner cylinder 54. Terminus 78 may be aligned with Luer lock 16b when inner cylinder 54 is rotated approximately 90° from the position shown in FIG. 3A, thereby permitting fluids to flow between syringe 24 (not shown in FIG. 3A) and infuser container 26 (not shown in FIG. 3A). Bottom surface 82 of inner cylinder 54 is adapted to provide a fluid tight seal with inner bottom surface, 84, of outer cylinder 38 as inner cylinder 54 is rotated within outer cylinder 38.

Inner ridge, 86, in outer cylinder 38 keeps inner cylinder 54 in place when inner cylinder 54 is rotated. In particular, bottom surface 82 of inner cylinder 54 is maintained in contact with bottom surface 84 of outer cylinder 38 such that liquids may pass from channel 76 to Luer locking device 16c and into infuser container 26 without escaping around the surface of inner cylinder 54. Inner cylinder 54 may be fabricated from a compressible polymer capable of being forced past ridge 86 during assembly of the apparatus, the inner ridge providing sufficient resistance to prevent the inner cylinder from being withdrawn once fully seated within the outer cylinder. A plastic or metal insert may be used to achieve a similar result.

Figure 3C:
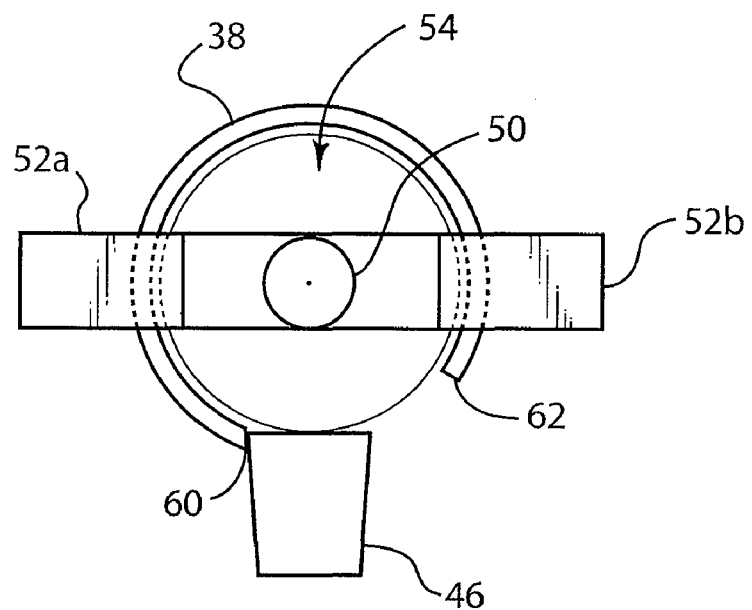
Figure 3D:
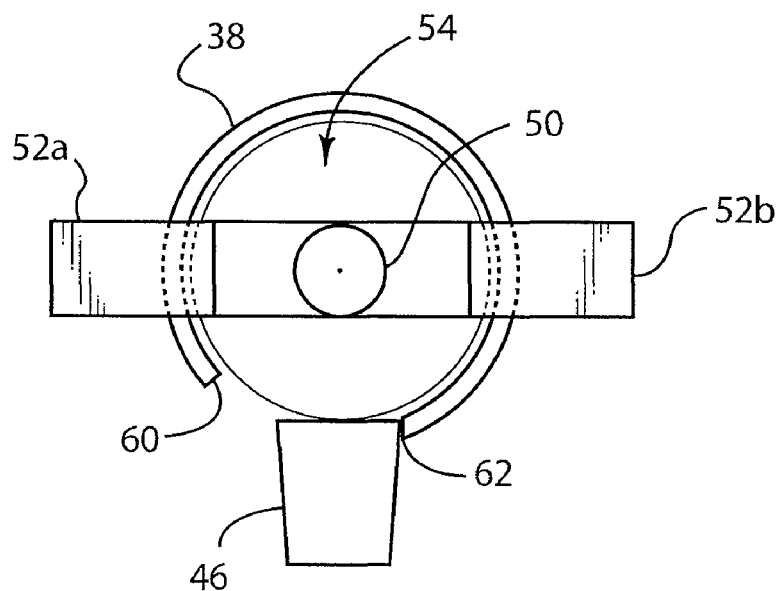
FIG. 3D is a schematic representation of a top cross section view thereof, illustrating the vial holding/piercing/transferring device being rotated 90° with respect to the three-way valve.

FIG. 3B is a schematic representation of a bottom cross section view of three-way valve 14 and vial holding/piercing/transferring device 18 shown in FIG. 3A hereof. FIG. 3C is a schematic representation of a top cross section view of three-way valve 14 and vial holding/piercing/transferring device 18 shown in FIG. 3A hereof, while FIG. 3D is a schematic representation of a top cross section view of three-way valve 14 and holding/piercing/transferring device 18 shown in FIG. 3A hereof, illustrating vial holding/piercing/transferring device 18 being rotated 90° with respect to outer cylinder 38. In use, the embodiment of the present invention described in FIGS. 2-3D hereof will be similar to that of apparatus 10 illustrated in FIG. 1 hereof which is described in the EXAMPLES set forth hereinbelow, except that the desired fluid connections are made by rotation of the inner cylinder with respect to the outer cylinder, as opposed to operating valve handle 37 on the three-way valve illustrated in FIG. 1 hereof; that is, connections between vial 20 and syringe 24, and alternatively between syringe 24 and infuser container 26.

Having generally described the present apparatus and method, additional details thereof are described in the following EXAMPLES.

Example 1

Medication Dilution:

Returning to FIG. 1, in order to dilute a concentrated dose 34 of medication contained in vial 20, syringe 24 would either be purchased having a chosen quantity of diluent 32, or the user would fill the syringe with the chosen quantity of diluent before attaching the syringe to Luer lock 16b. Vial 20 is attached to vial holding/piercing/transferring device 18, and valve handle 37 of three-way valve 14 is adjusted such that the fluid connection between port 12a and port 12b is open. The diluent in syringe 24 is then transferred to vial 20. After an appropriate mixing period for the two liquids, perhaps with some mechanical agitation thereof, the resulting diluted medication is drawn into syringe 24 from vial 20, and the fluid connection between port 12b and port 12c is opened using valve handle 37. The diluted medication is then transferred into infuser container 26.

Example 2

Medication Dissolution:

A similar procedure would be invoked for dissolving medications shipped as solids in vial 20 as that for diluting a concentrated liquid medication, and is described in EXAMPLE 1 hereinabove.

Example 3

Quantitative Transfer of Medications:

In the situation where it is desired to transfer a chosen quantity of medication from vial 20 to infuser container 26, an empty syringe 24 would be attached to port 12b, and the fluid connection between port 12a and port 12b of three-way valve 14 opened using valve handle 37. A chosen quantity of fluid would be drawn into syringe 24 from vial 20 as measured by graduation marks 40 on syringe 24. The fluid connection between ports 12b and 12c would then be opened and the fluid transferred between syringe 24 and infuser container 26.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for transferring medications from a vial into an infuser container having a fill port, which comprises in combination:

a three-way valve having a first port, a second port and a third port, wherein said three-way valve comprises:
a hollow cylinder having an open end and a closed end, a wall having an inner surface, and the closed end having an inner surface;
means for transferring medications through the wall of said hollow cylinder through the second port;
means for transferring medications through the closed end of said hollow cylinder through the third port;
a solid cylinder having an outer surface and adapted to rotate within said first cylinder such that medications do not flow between the outer surface of said solid cylinder and the inner surface of the cylindrical wall, and between the outer surface of said solid cylinder and the inner surface of the closed end of said hollow cylinder, said solid cylinder further comprising: means for transferring medications from said vial through the first port to a first duct in said solid cylinder adapted for permitting medications to pass between said vial and said means for transferring medications through the wall of said hollow cylinder, and means for transferring medications through a second duct in said solid cylinder for permitting medications to pass between said means for transferring medications through the closed end of said hollow cylinder and said means for transferring medications through the wall of said hollow cylinder; and means for rotating said solid cylinder relative to said hollow cylinder;

means for connecting said vial to the first port such that medications can be transferred between said vial and said three-way valve;

a syringe;

means for connecting said syringe to the second port such that medications can be transferred between said syringe and said three-way valve; and means for connecting the fill port of said infuser container to the third port of said three-way valve such that medications can be transferred between said three-way valve and said container.

2. The apparatus of claim 1, further comprising a one-way valve such that materials are only transferred into said infuser container from the third port of said three-way valve.

3. The apparatus of claim 1, wherein said means for connecting said vial to the first port of said three-way valve such that materials can be transferred between said vial and said three-way valve, comprises means for holding said vial and means for penetrating said vial.

4. A method for transferring solid medications in a vial into an infuser container having a fill port, which comprises the steps of:

connecting the vial to one port of a three-way valve;

connecting a syringe containing an effective amount of solvent for dissolving the solid medication to a second port of the three-way valve;

connecting the infuser to the third port of the three-way valve;

transferring the solvent from the syringe to the vial through a pathway in the three-way valve connecting the syringe with the vial, thereby forming a solution;

withdrawing the solution from the vial into the syringe through the pathway in the three-way valve connecting the syringe with the vial; and transferring the solution from the syringe to the infuser container through a pathway in the three-way valve connecting the syringe with the fill port of the infuser container.

5. The method of claim 4, wherein the infuser container comprises an elastomeric container.

6. The method of claim 5, wherein the fill port of the elastomeric container includes a one-way valve such that materials are only transferred into the infuser container.

7. The method of claim 4, wherein the vial comprises a plug adapted to be pierced for transferring materials into and out of the vial, and said step of connecting the vial to one port of the three-way valve is achieved by using means for holding the vial and means for piercing the plug.

8. A method for diluting liquid medications in a vial and transferring the diluted medications into an infuser container having a fill port, which comprises the steps of:

connecting the vial to one port of a three-way valve;

connecting a syringe containing a chosen amount of diluent to a second port of the three-way valve;

connecting the infuser to the third port of the three-way valve;

transferring the diluent from the syringe to the vial through a pathway in the three-way valve connecting the syringe with the vial, thereby forming a solution;

withdrawing the solution from the vial into the syringe through the pathway in the three-way valve connecting the syringe with the vial; and transferring the solution from the syringe to the infuser container through a one-way pathway in the three-way valve connecting the syringe with the fill port of the infuser container.

9. The method of claim 8, wherein the vial comprises a plug adapted to be pierced for transferring materials into and out of the vial, and said step of connecting the vial to one port of the three-way valve is achieved using means for holding the vial and means for piercing the plug.

10. A method for transferring liquid medications in a vial to an infuser container having a fill port, which comprises the steps of:

connecting the vial to one port of a three-way valve;

connecting an empty syringe to a second port of the three-way valve;

connecting the infuser to the third port of the three-way valve;

transferring the liquid medication from the vial to the syringe through a pathway in the three-way valve connecting the vial with the syringe; and transferring the liquid medication from the syringe to the infuser container through a one-way pathway in the three-way valve connecting the syringe with the fill port of the infuser container.

11. The method of claim 10, wherein the vial comprises a plug adapted to be pierced for transferring materials into and out of the vial, and said step of connecting the vial to one port of the three-way valve is achieved using means for holding the vial and means for piercing the plug.

* * * * *